United States Patent
Reddick et al.

(10) Patent No.: US 6,981,001 B1
(45) Date of Patent: Dec. 27, 2005

(54) METHOD AND SYSTEMS FOR DEFAULT MAPPING MECHANIZATION

(75) Inventors: Charlie Reddick, Palatka, FL (US); C. W. Garris, Peachtree City, GA (US); Robert A. Cole, Helena, AL (US); Robert M. Ingman, Peachtree City, GA (US); Roy E. Glascoe, Jr., Alpharetta, GA (US); Paul J. Mankowski, Marietta, GA (US)

(73) Assignee: BellSouth Intellectual Property Corporation, Wilmington, DE (US)

( * ) Notice: Subject to any disclaimer, the term of this patent is extended or adjusted under 35 U.S.C. 154(b) by 900 days.

(21) Appl. No.: 09/957,988

(22) Filed: Sep. 21, 2001

(51) Int. Cl.[7] .................................. G06F 17/30
(52) U.S. Cl. ........................ 707/104.1; 707/2; 707/3; 707/6; 715/507; 705/3
(58) Field of Search ....................... 707/1, 2, 3, 10, 707/100, 104.1, 6; 701/29, 30, 208, 213; 705/3; 455/456.6; 342/457; 715/506, 507, 715/508, 516

(56) References Cited

U.S. PATENT DOCUMENTS

| | | | |
|---|---|---|---|
| 5,748,148 A * | 5/1998 | Heiser et al. ................ 342/457 |
| 6,154,727 A * | 11/2000 | Karp et al. ..................... 705/3 |
| 6,393,415 B1 * | 5/2002 | Getchius et al. ............... 707/2 |
| 6,526,284 B1 * | 2/2003 | Sharp et al. ............. 455/456.6 |
| 6,542,814 B2 * | 4/2003 | Polidi et al. ................ 701/208 |
| 6,556,899 B1 * | 4/2003 | Harvey et al. ................ 701/29 |
| 6,567,822 B1 * | 5/2003 | Cudahy et al. .......... 707/104.1 |
| 6,611,739 B1 * | 8/2003 | Harvey et al. ................ 701/29 |
| 6,665,611 B1 * | 12/2003 | Oran et al. .................. 701/213 |
| 6,718,263 B1 * | 4/2004 | Glass et al. ................. 701/213 |
| 6,757,693 B2 * | 6/2004 | Taniguchi et al. ....... 707/104.1 |
| 6,801,915 B1 * | 10/2004 | Mack .......................... 707/100 |
| 2002/0107837 A1 * | 8/2002 | Osborne et al. ............... 707/2 |

OTHER PUBLICATIONS

Tele Atlas North America, Inc. Digital Maps, Traffic Solutions: http://www.etak.com, "Tele Atlas"; Internet Download Aug. 29, 2001.

Tele Atlas North America, Inc. Digital Maps, Traffic Solutions: http://www.etak.com/geoprod.html, "Geocoding Services"; Internet Download Aug. 29, 2001.

Telcordia—Common Language® Locate It® System: Product Overview: http://www.telcordia.com/resources/commonlang/locateit/index.html, "Common Language® Address Analysis System (LocateIt® System): Product Overview"; Internet Download Dec. 19, 2001.

Telcordia—Common Language® Locate It® System: Product Description: http://www.telcordia.com/resources/commonlang/locateit/product_description.html, "Common Language® Address Analysis System (LocateIt® System): Product Description"; Internet Download Dec. 19, 2001.

(Continued)

*Primary Examiner*—Shahid Al Alam
(74) *Attorney, Agent, or Firm*—Cantor Colburn LLP

(57) ABSTRACT

Methods and systems are provided for acquiring and assembling customer facility location data from multiple sources. The customer facility location data is subsequently used for the automated dispatching of service technicians in a resource-efficient fashion.

18 Claims, 6 Drawing Sheets

OTHER PUBLICATIONS

Telcordia—Common Language® Locate It® System: Product Services: http://www.telcordia.com/resources/commonlang/locateit/product_services.html, "Common Language® Address Analysis System (LocateIt® System): Product Services"; Internet Download Dec. 19, 2001.

Telcordia—Common Language® Locate It® System: Product Solutions: http://www.telcordia.com/resources/commonlang/locateit/product_solutions.html, "Common Language® Address Analysis System (LocateIt® System): Product Solutions"; Internet Download Dec. 19, 2001.

Telcordia—Common Language® Locate It® System: Product News: http://www.telcordia.com/resources/commonlang/locateit/about_us.html, "Common Language® Address Analysis System (LocateIt® System): Product News"; Internet Download Dec. 19, 2001.

Telcordia—Telcordia—"Unisys World" Article: http://www.telcordia.com/resources/commonlang/locateit/articles/at_a_glance.html, "Telcordia, Unisys® Develop Object-Data Base Management System"; Internet Download Dec. 19, 2001.

* cited by examiner

METHOD AND SYSTEMS FOR DEFAULT MAPPING MECHANIZATION

CROSS-REFERENCES TO RELATED APPLICATIONS

United States Utility Patent Application by C. Reddick et al., filed on the same date as this application and entitled "Methods and Systems for Latitude/Longitude Updates," is hereby incorporated by reference.

FIELD OF THE INVENTION

The present invention relates generally to the field of automated dispatching of personnel. More particularly, the present invention relates to systems and methods for implementing a default mapping mechanization service.

COPYRIGHT NOTICE

A portion of the disclosure of this patent document contains material which is subject to copyright protection. The copyright owner has no objection to the facsimile reproduction by anyone of the patent document or the patent disclosure, as it appears in the United States Patent and Trademark Office patent file or records, but otherwise reserves all copyright rights whatsoever.

BACKGROUND

Telephone company service technicians are dispatched to customer sites for a variety of reasons. For instance, technicians may be dispatched because a new service connection may need to be established, the cause of a power outage may need to be isolated, or a communications line may need to be located.

Conventionally, telephone company service technicians are dispatched to a customer site to perform the repair or service as indicated by a work order. When a technician completes this work, the technician calls for instructions as to the next task. A dispatcher then provides the service technician with the next work order, which specifies a customer location and the service required. A dispatcher may be a person or a computer system. An important goal of the dispatching process is to provide quality customer service.

Quality customer service requires a balancing of response times and priorities. Thus technicians need to be dispatched such that they are responsive to customer needs in a timely fashion. Additionally, the dispatch must allow for flexibility, so that a technician can be dispatched to high priority repair events.

One problem encountered with conventional dispatching processes is that the resulting dispatched work order can cause technicians to waste time driving. For example, a technician may first work at a site on Smith Road, then be dispatched to Jones Street, and subsequently dispatched to a different customer site on Smith Road. That technician's time would be more efficiently utilized by dispatching the technician to the two Smith Road sites just before or just after addressing the Jones Street work order. The additional driving time incurred by the technician is time that could have been used in servicing other customers. Thus a resource (i.e., a technician's time) is wasted and the resolution of a customer site telephone problem or service issue is unnecessarily delayed.

Automated systems for dispatching technicians have been developed by various companies. For example, some conventional systems provide technicians with work orders for customer sites that are within the vicinity of each other. Such conventional systems accept work order requests from technicians in the field. The system then looks at all of the pending work orders. From the locations of pending work orders and the current location of the technician, the system determines which customer site is closest to the technician's current locale. The system makes this determination using locational data, based upon latitude and longitude coordinates, to produce the tightest possible dispatch for the technician.

Common problems encountered, though, include instances in which latitude and longitude locational information is unavailable for the work site in question (e.g., a new sub-division), and instances in which the address of the work site is erroneous. In such cases, no latitude and longitude location information would be discovered within a commercial database.

In a conventional method, a computer system (such as LocateIt, which is distributed by Telcordia Technologies) accesses a commercial database that contains location information, such as latitude and longitude coordinates, for many businesses and residences. An example of such a commercial data base is one provided by Geographical Data Technology and known as the GDT database.

Using such a conventional method, a conventional automatic dispatching system queries the LocateIt system whenever latitude and longitude information is needed to identify a customer location. LocateIt, in turn, queries the geographical database.

LocateIt subsequently returns to the system the requested locational information for the customer site in question.

Correct location information using this conventional system is obtained in only 68% of the queries. Thus, using conventional techniques, a technician is still very likely to have unnecessary drive times. A correct location determination rate above 90% is desirable.

One method to increase the likelihood that correct location information would be found requires personnel to drive to customer sites, determine the site latitude and longitude information via a Global Positioning Satellite (GPS) receiver, and then log this location information. Although such a back up method produces accurate information regarding customer locations, driving to each customer site is a very time consuming, and thus costly, process.

What is needed are methods and systems that overcome the shortcomings of conventional systems. Such methods and systems should provide additional advantages, including cost effectiveness and ease of implementation.

SUMMARY

An embodiment of the present invention provides methods and systems for the efficient acquisition and conversion of customer site address and telephone network interface information to customer site locational information, such as latitude and longitude data. Implementations of the present invention comprise at least one of a method, a process, a system, an apparatus, a computer readable medium, and a data stream.

Embodiments of the present invention provide for populating empty or null locational data fields in a dispatching system with locational data, such as latitude and longitude values. In one embodiment, a file of incomplete location records is received by a receiver component (such as a computer). An incomplete record, i.e., a record containing a null location data field, is then extracted from the file via an extractor component. A non-null field, such as a customer site address, is then extracted or parsed by a parsing component from the incomplete record. A non-null extracted field value, which is used as a search key, may comprise a street address, a cross-connect identifier, a wire center identifier, and/or an allocation area identifier. The parsed data is used as a key to index into a data repository comprising records that contain both the parsed field (i.e., the customer site address) and a locational value. A locational value may comprise latitude and longitude coordinates. Examples of data repositories include data bases and flat files. When a record with a field matching the extracted/parsed field value is found via a search of the data repository, a copy of that record is written to a file known as a match file. In alternative embodiments, the data repository comprises at least two databases. One such embodiment includes a local database and a wire center database.

In one embodiment, the match file is forwarded to a follow-on processor electronically, using a file transfer protocol as an example electronic transfer mechanism. Alternatively, the match file is first stored on a medium, such as a floppy disk or tape, and then forwarded to the appropriate medium reading device for the follow-on processor.

In alternate embodiments, a data repository comprises a database or a flat file. Data repositories are characterized by the type of data fields contained within records stored in the data repository. For instance, a wire center database and a cross-connect database contain customer site records having at least wire center identifier and cross-connect identifier fields, respectively.

Embodiments of the present invention offer many advantages, including substantially increasing the hit rate of latitude and longitude determinations for customer site location records stored within a data repository. By increasing the hit rate, the present invention provides more accurate customer site location results for use in the automatic dispatching of service technicians. Furthermore, by providing more accurate location information, technicians may be dispatched to service customer sites that are more centrally located. Service technicians spend less time driving between work sites, and therefore are able to respond to customers' requirements in a more timely fashion.

Embodiments of the present invention also enable a supervisor to decrease the number of workers that need to be assigned to location data look up and entry tasks. These workers are then made available to perform other tasks.

Additional objects, advantages, and novel features of the invention will be set forth in part in the description which follows, and in part will become more apparent to those skilled in the art upon examination of the following, or may be learned by practice of the invention.

DETAILED DESCRIPTION

In the following discussion of embodiments of the present invention, numerous specific details are set forth in order to provide a thorough understanding of the present invention. The present invention may be practiced without some or all of these specific details. In other instances, well known process operations have not been described in detail in order not to unnecessarily obscure the present invention.

Figure 1:
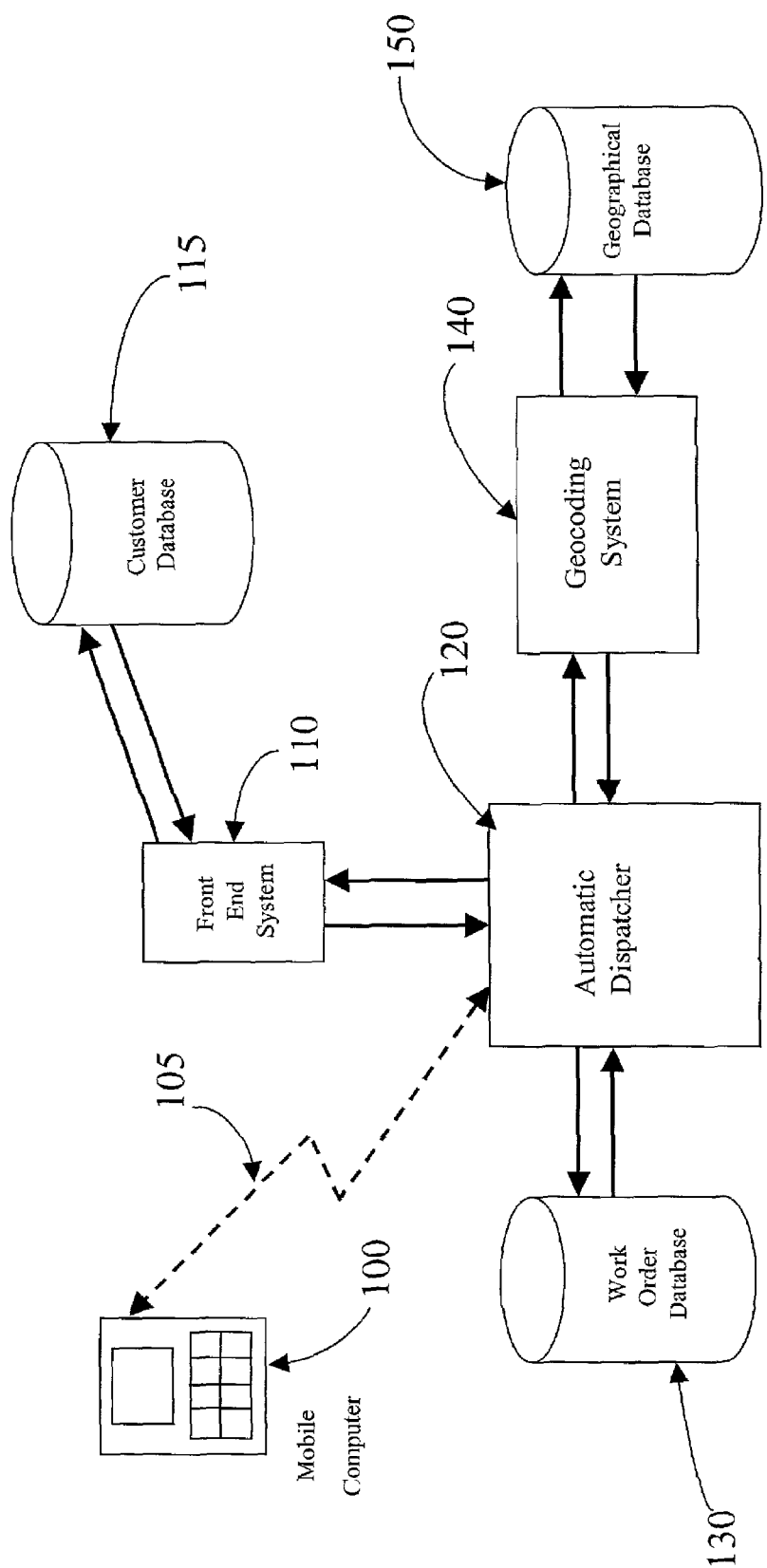
FIG. 1 illustrates a conventional automated dispatch system.

FIG. 1 illustrates a conventional (prior art) technique for providing customer location data for use in the dispatching of service technicians. In FIG. 1, a technician using a communications device 100, such as a mobile computer, contacts an automated dispatcher 120 to request the technician's next work order. Communication between the mobile computer 100 and the automated dispatcher system 120 takes place via a radio frequency (RF) link 105. The automated dispatcher 120 shown is referred to as the Integrated Dispatch System (IDS). The IDS searches a list of pending work orders for a work order for the customer site nearest the technician's current location by comparing latitude and longitude values of "pending" work sites to that of the current site.

The automated dispatcher 120 comprises a computer system that determines which work order should be assigned to the technician. Since the technician's current location is stored on the automated dispatcher 120, when a work order request from the technician arrives at the automated dispatcher 120, the automated dispatcher 120 can compare the technician's current location to the locations of all customers with pending work orders. Pending work orders are records that contain customer site location fields and are stored in a work order database 130. Customer site locations are based upon latitude and longitude coordinates. The pending work order of the customer site determined by the automated dispatcher 120 to be the closest to the technician's current location is assigned to the service technician. The automated dispatcher 120 then dispatches the technician by forwarding the work order via the RF link 105 to the requesting technician.

A front-end system 110, such as the BellSouth Loop Maintenance Operating System (LMOS), forwards work requests from upstream trouble reporting and service order systems to an automated dispatcher 120. The front-end system 110 constructs a work order for the automated dispatcher 120 by first querying a customer database 115 for the addresses of customer sites that require service. The customer database 115 contains records having customer site address, allocation area, and wire center information fields. In one embodiment, a commercial database is utilized as a customer (records) database 115.

The automated dispatcher 120 constructs a list of pending work orders by first querying an address geocoding system 140. Automated dispatcher 120 provides a street address of a customer site to the geocoding system 140, which subsequently queries a commercial geographical database 150. An example geocoding system 140 is known as LocateIt, which is a Telcordia provided computer system that executes software for accessing a commercial geographical database 150, and from that database determines a latitude and longitude for a customer site. One such commercial geographical database 150, called the GDT database, is provided by Geographical Data Technology. The GDT database contains locational data (i.e., latitude and longitude coordinates) for customer addresses throughout the region covered by the service technicians.

The query response from the geographical database 150 contains locational information for a customer site address. The locational data is propagated back from the geographical database 150 through the geocoding system 140 to the automated dispatcher 120. At this point, the automated dispatcher 120 adds the locational data to the work order record associated with that customer site and contained within the pending work order list. The resulting work order record is added to the work order database 130.

By accessing the commercial geographical database 150, a higher percentage of work orders can be provided with customer site locational data. Without this location data, the automated dispatcher 120 cannot automatically dispatch service technicians. The fallback position is to manually dispatch technicians, if the automated dispatcher 120 cannot perform an automated dispatch. This is a slow and personnel-intensive task, that often results in technicians being inefficiently assigned to work orders.

For a variety of reasons, such location information is not available in commercial databases for all possible sites. For instance, new construction of both commercial and residential sites renders a tremendous amount of geographical data in commercial databases obsolete. As a consequence, periodic reports of sites with unknown geographic coordinates (i.e., latitude and longitude values) must be generated and manually edited.

An embodiment of the present invention carries out various functions, including automating the process of providing latitude and longitude values for a Default Mapping Report (DMR) 205. The DMR 205 comprises an electronic report or file which is produced via report generation facilities within the automated dispatcher 120. The DMR 205 contains customer site addresses for which no associated locational data has been found within any of the commercial databases, such as the GDT database. One such embodiment is illustrated in FIG. 2.

Figure 2:
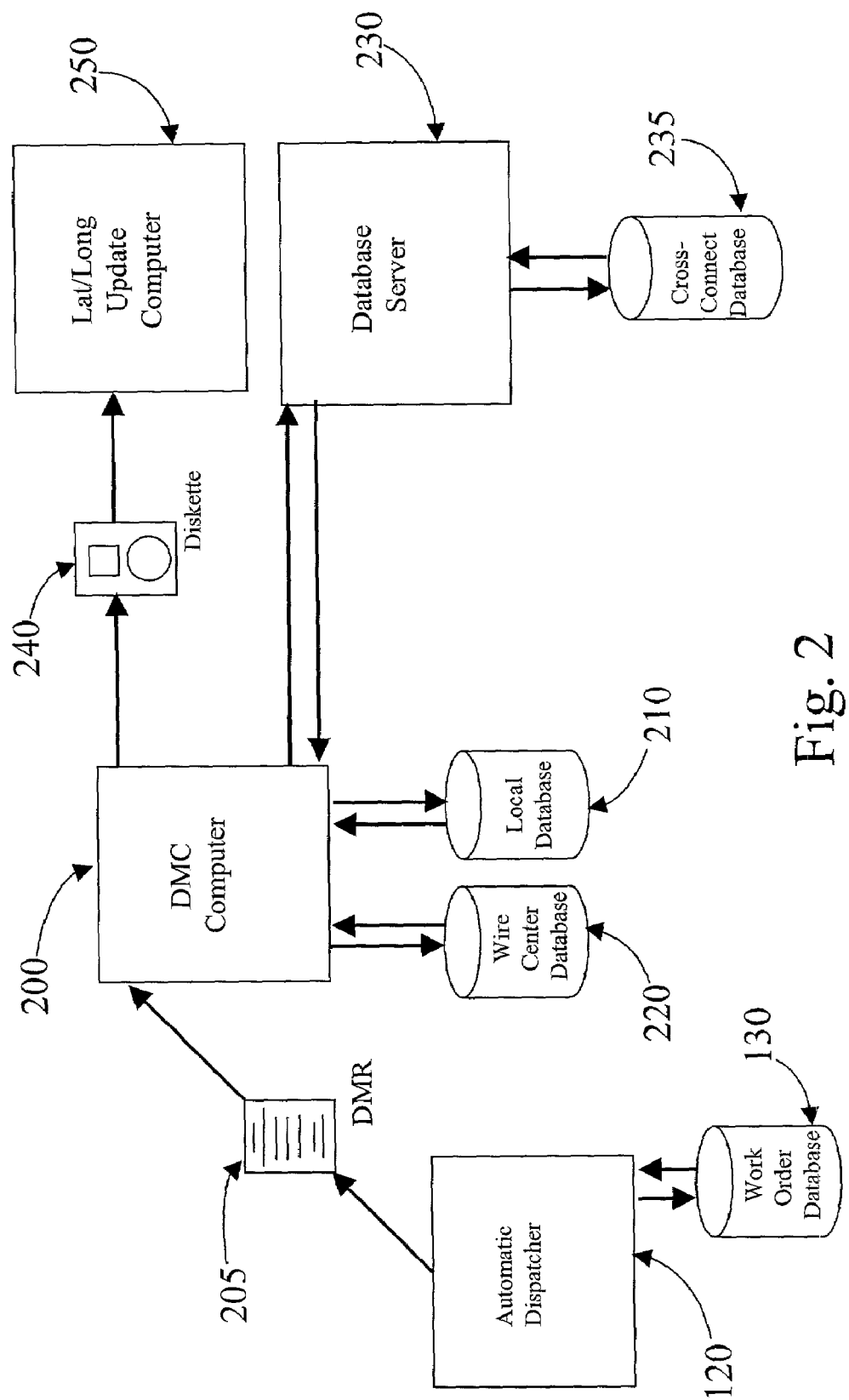
FIG. 2 illustrates an embodiment of the present invention for providing a default mapping conversion service.

In the exemplary embodiment of the present invention shown in FIG. 2, a Default Mapping Conversion (DMC) computer 200 hosts software for reading an electronic copy of a Default Mapping Report (DMR) 205. The DMC computer 200 also queries data repositories 210, 220 in order to supply the missing customer site locational data for the DMR 205 records.

In the embodiment shown, the DMC computer 200 receives a softcopy version of the DMR 205 from automated dispatcher 120. The DMR 205 comprises incomplete records that contain fields such as a task number (or work order number), customer street address, a wire center identifier, and a cross-connect identifier. The record is incomplete because it contains an empty or null field for customer site geographical location data. An example of customer site geographical location data includes latitude and longitude coordinates. A wire center identifier is an alphanumeric that is associated with a wire center facility. A cross-connect identifier is an alphanumeric that is associated with a particular communications switch such as an AT&T DACS (Digital Access Cross-connect Switch). In alternate embodiments, a DMR 205 further comprises an allocation area identifier. An allocation area is a geographical region that roughly corresponds to one thousand phone numbers. The identifier of an allocation area is also an alphanumeric value.

In the embodiment shown, a DMC computer 200 communicates with a local database 210 and a wire center database 220. The local database 210 stores information comprising street addresses, block addresses (which are numbers associated with a group of buildings), and latitude and longitude location values for customer sites. The wire center database 220 stores information comprising street addresses, wire center identifiers, and latitude and longitude location values for customer sites. The databases 210 and 220 may be remotely located. Other embodiments include interfacing the DMC computer 200 to a data repository comprising at least two databases (or flat files). In other words, additional internal, external and remotely located databases (and/or flat files), comprising customer and telecommunications network information, such as allocation areas, may be interfaced to the DMC computer 200. In another embodiment, the DMC computer 200 may be interfaced to a data repository, comprising at least one database (and/or flat file).

Continuing with the description of an embodiment shown in FIG. 2, the DMC computer 200 also interfaces to a database server 230. An example database server 230 is a BellSouth system known as the Internet Geocoder. The database server 230 interfaces to a cross-connect database 235, which contains information records on customer site addresses and associated cross-connect identifiers. Cross-connect identifiers reference telephone system network elements (i.e., switches). The DMC computer 200 queries the database server 230 for latitude and longitude values associated with a task number and cross-connect identifier. The database server 230, in turn, queries a cross-connect database 235, and returns the response (containing the latitude and longitude coordinates associated with the task and cross-connect values) to the DMC computer 200.

For those queries in which a locational value (comprising latitude and longitude coordinates) is found for the customer site in question, the DMC computer 200 stores the complete customer information, which at this point includes the missing customer site location values. Once the entire electronic DMR 205 is processed, the DMC 200 forwards a file containing the complete customer information, including the customer site location information, to a follow-on processor for further processing. The Lat/Long Update computer 250 shown in FIG. 2 is an example follow-on processor, which takes the completed customer information file, known as a match file, and subsequently reformats the match file records and merges them into a work order database 130, such as the Telcordia Force database.

The work order database 130 stores work order records, which comprise fields such as a customer site address field, a customer site geographical location field, a work order number field and a field for a description of the service issue. The automated dispatcher 120 uses the values from a customer site geographic location field of a work order record to determine the customer site nearest a technician's current work site and then automatically dispatches the technician to the nearest customer site (i.e., the automated dispatcher 120 then assigns the technician's next work assignment to be the work order associated with the nearest customer site).

FIG. 2 illustrates a transfer mechanism in which the complete customer information file is forwarded as a floppy disk or diskette 240 to a Lat/Long Update computer 250. Such a mechanism is an option in an environment with network security concerns in which physical connectivity is not permitted between the Local Area Network (LAN) segments that host the DMC 200 and Lat/Long Update 250 computers. Alternate embodiments, in which such stringent security requirements are not mandated, allow for implementations using file transfer techniques, such as the File Transfer Protocol (FTP), or using data collaboration techniques, such as using a shared disk to which the DMC computer 200 writes and from which the Lat/Long Update computer 250 reads.

Figure 3:
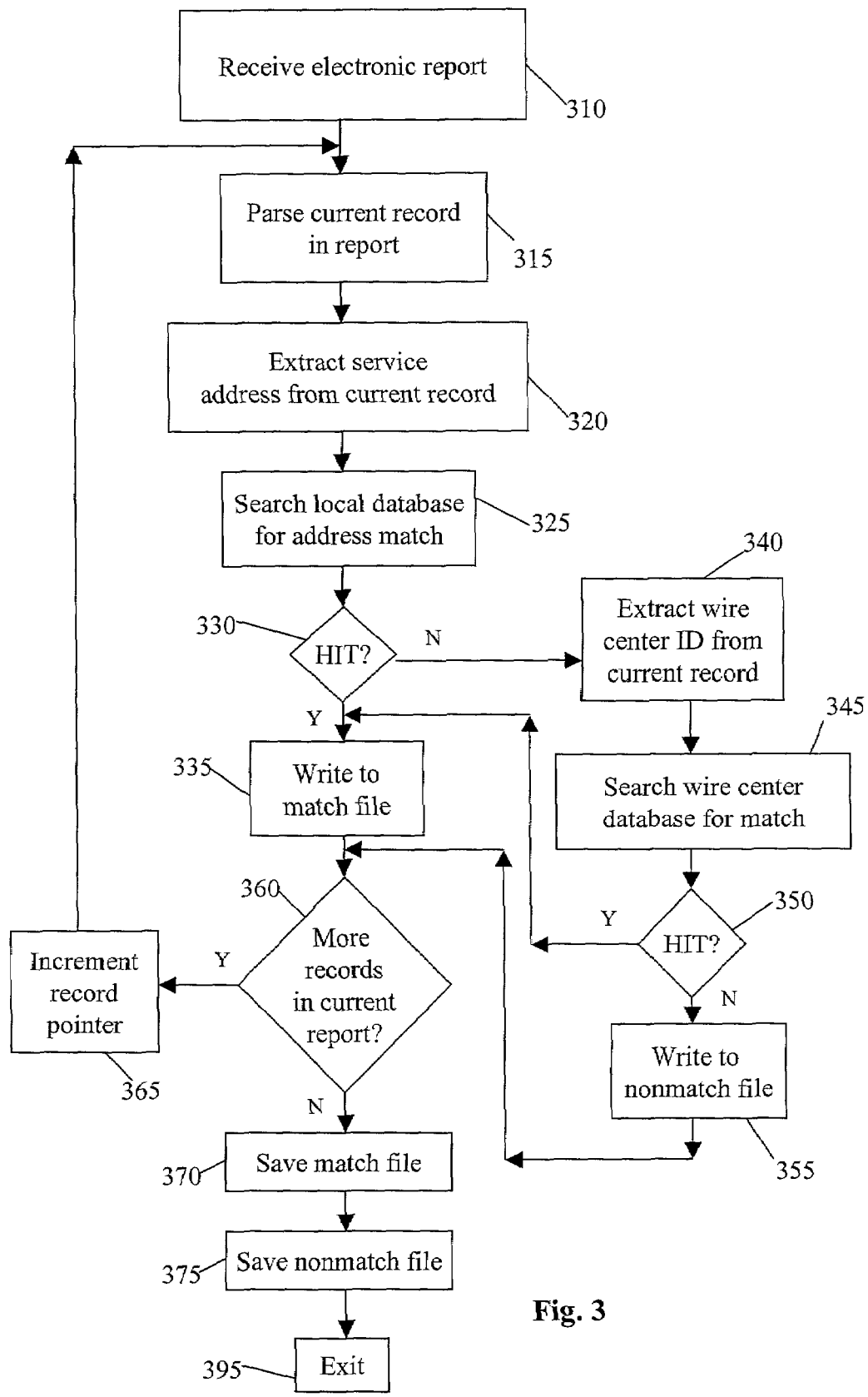
FIG. 3 comprises a flow chart of an embodiment of the present invention for producing match and nonmatch files.

An exemplary method of implementing an embodiment of the present invention is illustrated in the flow chart of FIG. 3. This method is executed on the DMC computer 200, which was previously described in reference to FIG. 2.

Referring to FIG. 3, at step 310 the DMC computer 200, via a receiver component, receives an electronic report, the DMR 205, from automated dispatcher 120. At step 315, the DMC computer 200, via an extractor component, extracts and parses the current record, which at this point is the first record (i.e., line) of the DMR 205, and then extracts or parses, via a parser component, the customer address from the current record in step 320. In one embodiment, the customer address is a street address. Note that each record in the DMR 205 is an incomplete record in that each record includes a customer site location field containing a null value.

DMC computer 200, at step 325, uses the extracted service address as a key to search a data repository, the local data base 210, for a record containing the customer service address and corresponding (non-null) locational information comprising latitude and longitude values. The local database 210 is populated with customer site location data that was acquired from GPS readings taken during previous customer site visits. This data often corresponds to newly constructed residential or commercial facilities.

In additional embodiments, at least two of a street address, a wire center identifier, a cross-connect identifier and an allocation area may be parsed/extracted from the current DMR 205 in step 320 and utilized as a key in searching the appropriate database in step 325. The "appropriate" database is a database that contains records having all of the search key fields.

Referring again to FIG. 3, if a hit or match is found in the local database 210 at step 330, then a copy of the local database record match (i.e., the match record) is written or inserted at step 335 into a match file that is stored on the DMC computer 200. The match file is a file which contains copies of records from the local database 210 which were found at step 330. An insertion means, such as a write( ) utility function, is utilized to perform step 335. Records are also added to the match file in steps 440 and 463 of FIG. 4, which is discussed later. The match file will ultimately contain completed records constructed from the incomplete customer site location records of the DMR 205. After the DMC computer 200 executes step 335, processing continues at step 360, which will be discussed later.

If a hit or match is not found at step 330, then the DMC computer 200, via a parser component, parses the current record of the DMR 205 to obtain a wire center identifier value from the current DMR 205 record at step 340. The DMC 200 in step 345 searches a data repository (in this embodiment, the wire center database 220) for a record having the same wire center identifier and street address as the current record of the DMR 205.

Regarding steps 340 and 345, in alternative embodiments, a cross-connect identifier or an allocation area identifier may be parsed/extracted, via a parser component, from the current DMR 205 record in step 340 and used as a key in searching an appropriate database in step 345. Further embodiments of steps 320 and 325 include implementations in which multiple fields may be parsed/extracted and used as a search key for the appropriate database. The "appropriate" database is a database that contains records having all of the search key fields.

If a hit or matching wire center database record is found at step 350, then the DMC computer 200 writes a copy of that record to the match file in step 335. Processing then continues at step 360, which is discussed later.

Referring again to the embodiment shown in FIG. 3, if a hit or match is not found at step 350, then in step 355 the DMC computer 200 writes the current DMR 205 record to a nonmatch file. The nonmatch file is stored on the DMC computer 200 and contains DMR 205 records for which no customer site location information was found. Processing then continues at step 360, which is discussed next.

After executing step 335 or step 355, the DMC computer 200 determines whether more records exist in the DMR 205 at step 360. If more records exist in the DMR 205, then the DMC computer 200 increments the current record pointer in step 365 and returns to the processing loop which begins at step 315. Execution will continue within this processing loop until all records of the DMR 205 have been processed. If no further records exist in the DMR 205, as determined by the DMC computer 200 at step 360, then the DMC computer 200 saves the match file in step 370 and saves the nonmatch file in step 375. The DMC computer 200 exits processing at step 395.

Note that in an alternative embodiment, steps 340 through 355 are unnecessary. In such a case, if there were no "HIT" at step 330, processing would merely continue at step 360. And in other embodiments, different search keys may be extracted in step 340 and used to search an appropriate database in step 345.

The DMC computer 200 applies an additional level of processing to the nonmatch file created during the processing described in FIG. 3. This additional processing is the subject of FIG. 4, which shows a flow chart of an exemplary mechanism for further processing of the nonmatch file. The extra processing levels include accessing an additional database containing customer site location information and, as a last resort, affording a user the opportunity to manually supply missing location information.

Figure 4:
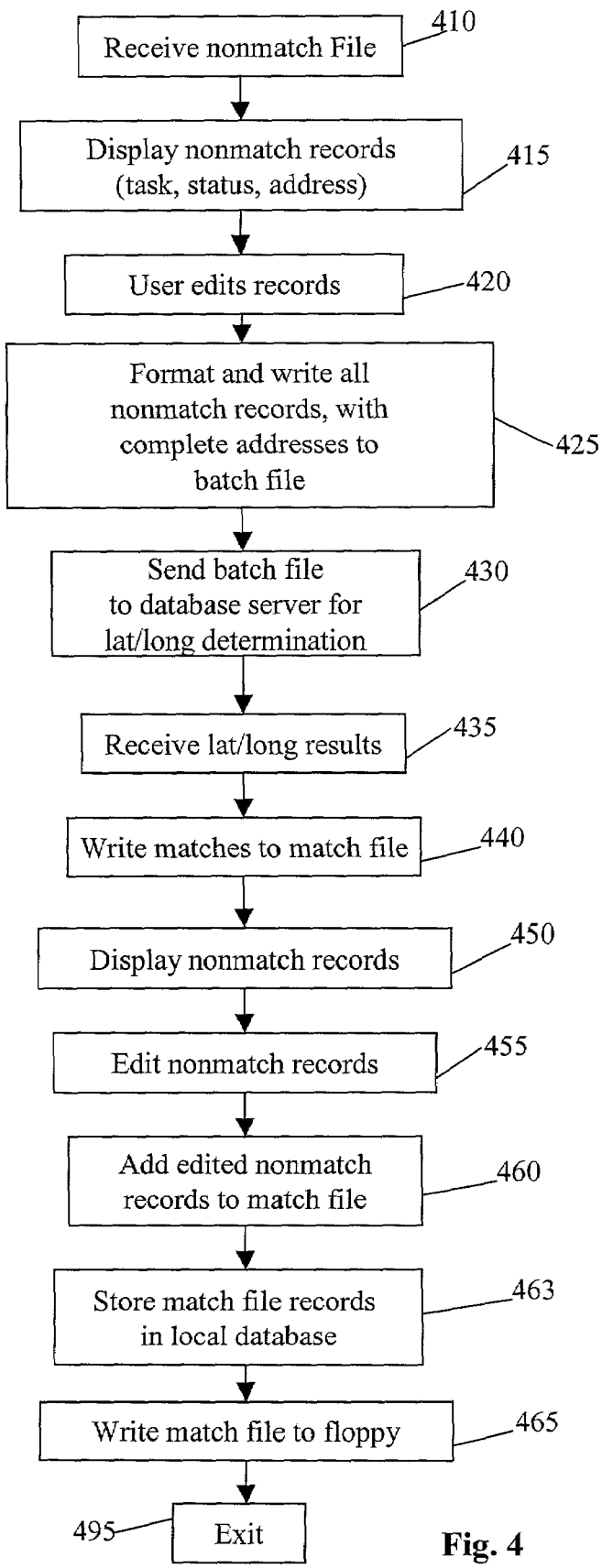
FIG. 4 comprises an embodiment of the present invention for converting nonmatch records to match file records.

Referring to FIG. 4, the DMC computer 200 receives the nonmatch file at step 410. The nonmatch file comprises records in which latitude and longitude location values for a customer site were not found during the process described in FIG. 3, above. Note that if customer site location values cannot be supplied at this stage, then technicians must be manually dispatched to address work orders for service issues at these customer sites.

The DMC computer 200 presents in a graphical user interface the records contained in the nomnatch file to a user at step 415, and allows the user to edit those records at step 420. At this point, the user edits these records either to correct erroneous customer addresses or to supply missing customer addresses. Nonmatch records that have a complete address are formatted and written to a batch file by the DMC computer 200 in step 425. In one embodiment, these records are formatted in a specific format used by the commercial geographic database company, but any format may be used. The DMC computer 200 subsequently forwards the batch file to the database server 230 at step 430 for a determination of latitude and longitude location values of the customer site corresponding to each nonmatch record within the batch file.

The DMC computer 200 receives the results from the database server 230 at step 435. Each resultant record returned from the database server 230 comprises a customer site address and a non-null location value (i.e., a latitude and longitude value). At step 440, the DMC computer 200 adds a copy of each resultant record to the match file, which was previously described in the discussion of FIG. 3.

If there are any customer work order records at this stage that still do not have latitude and longitude values (i.e., remaining nonmatch records), the DMC computer 200 will display those records on the DMC computer 200 at step 450. The user is again afforded the option of editing the remaining nonmatch records at step 455. The edits supplied here, however, are customer site location data i.e., latitude and longitude values), if known by the user. Remaining nonmatch records that are successfully edited at this point, such that the record contains a correct street address and a non-null location value, are also added by the DMC computer 200 to the match file at step 460.

Additionally, the DMC computer 200 at step 463 adds a copy of each match file record to the local database 210. Thus these records will not appear in a future DMR 205.

At this point, the DMC computer 200 writes the match file to a diskette 240 in step 465. In other embodiments, the match file may be written to a different media type, such as a magnetic tape or a CD-RW. The DMC computer 200 exits processing at step 495 of FIG. 4.

The storing of the final match file allows for the transfer of this file to follow-on processing systems, such as a Lat/Long Update computer 250, which provides subsequent or "follow-on" processing of the match file. A transfer mechanism utilizing media such as a diskette 240 (i.e., a floppy disk) is advantageous in an environment which requires the physical separation of the LANs on which a DMC computer 200 and a Lat/Long Update computer 250 reside. In embodiments having less stringent security requirements, the DMC computer 200 electronically transfers a final match file to at least one follow-on processor, such as a Lat/Long Update computer 250, or writes a final match file to a shared directory that may be accessed by follow-on processors. Follow-on processors apply subsequent or "follow-on" processing to the match file data.

A Lat/Long Update computer 250 utilizes the diskette 240, which contains a file of customer site addresses and non-null location value records (i.e., the match file). The diskette 240 is used to update a work order database 130 that includes customer site location information. As previously discussed, an example work order database 130 is the Force database, which is provided by Telcordia Technologies.

Figure 5:
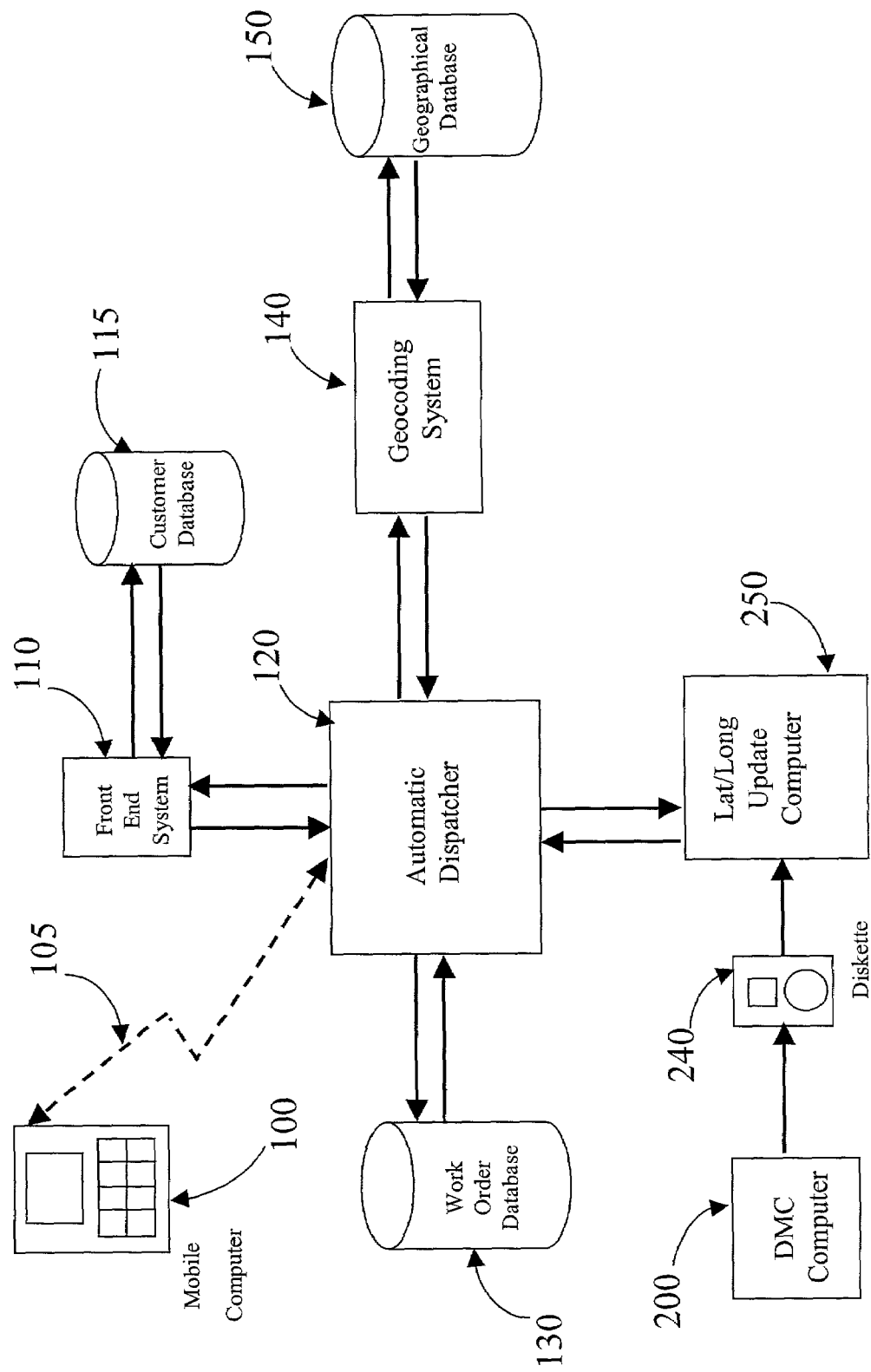
FIG. 5 illustrates an embodiment of the present invention for providing latitude and longitude updates.

As shown in FIG. 5, the DMC computer 200 stores a match file on a diskette 240, which is subsequently transferred to a Lat/Long Update computer 250. The Lat/Long Update computer 250 executes a terminal emulation package that is configured to automatically execute the work order database 130 graphical user interface (GUI). In one embodiment, a commercial software package, SilkTest, which was developed by Segue Software, Inc., is used for terminal emulation.

From within the terminal emulator, the Lat/Long Update computer 250 invokes scripts to automatically read records from the match file provided by floppy disk or diskette 240 and populate the appropriate input (text) fields of the customer database GUI. The Lat/Long Update computer 250 then invokes scripts which result in the input field values being formatted into customer site location records and added via the automated dispatcher 120 to the work order database 130.

Other systems that are co-located or networked with the Lat/Long Update computer 250 in FIG. 5 were discussed in regards to the prior art facility of FIG. 1. These systems include the automated dispatcher 120 and work order database 130, which are primarily responsible for providing a technician using a mobile computer 100 with the technician's next service assignment via the RF link 105. The geocoding system 140 and associated commercial geographical database 150 provide an additional source for customer geographical location information, beyond the customer database 115. The Lat/Long Update computer 250 receives a match file created by the Default Mapping Conversion process that is implemented on the DMC computer 200. This match file is stored on a diskette 240 in one embodiment.

Figure 6:
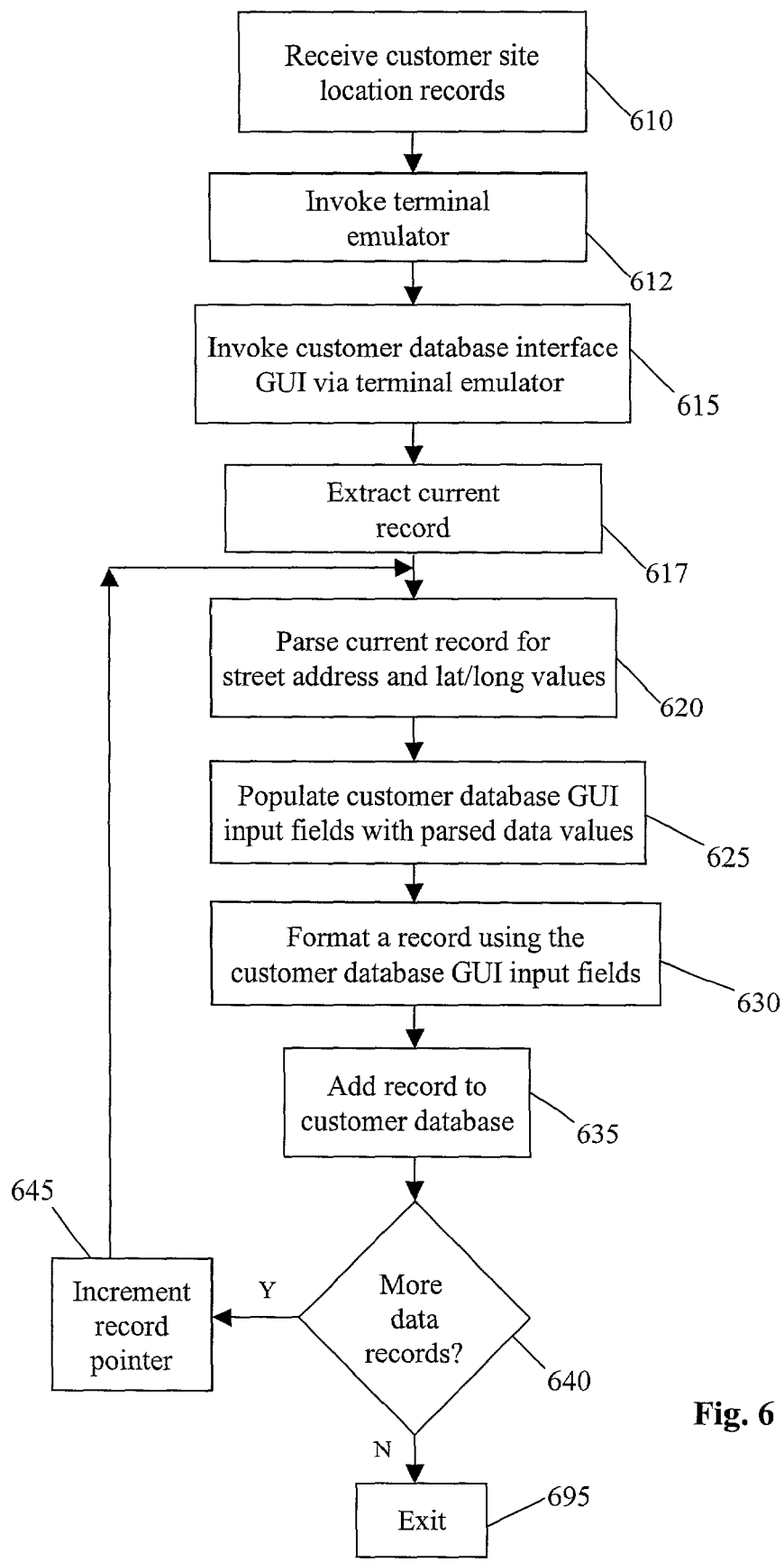
FIG. 6 comprises a flow chart of an embodiment of the present invention for producing latitude and longitude updates.

FIG. 6 comprises a flow chart of an embodiment of the present invention for producing latitude and longitude updates. This flow chart is implemented in computer software executed on the Lat/Long Update computer 250 shown in FIG. 5.

In FIG. 6, the Lat/Long Update computer 250 receives, via a receiver component, customer site location records from the DMC computer 200 at step 610. In the embodiment shown, customer site location records comprise customer street address and location (i.e., latitude and longitude) values. In one embodiment, records are received from a match file stored on a diskette 240. Other embodiments are available in which the match file is stored on a different medium or electronically transferred from the DMC computer 200 to the Lat/Long Update computer 250.

At step 612 the Lat/Long Update computer 250 invokes a terminal emulation application, which in turn logs into a data repository, the work order database 130, and executes the customer database GUI and scripts for adding customer site location records to the work order database 130 at step 615. The customer site location records are output to a GUI display device for a user to monitor the terminal emulation application's status. In alternative embodiments, other data repositories are utilized. Common data repositories include databases and flat files.

After receiving, via a receiver component, the customer site location records (i.e., "first" records) in step 610, the Lat/Long Update computer 250 extracts, via an extractor component, the current record in step 617. The Lat/Long Update computer 250 then parses the current record for street address value, using a first parser component, and a location value, using a second parser component in step 620. In one embodiment, location values comprise a latitude and a longitude.

In step 625, the Lat/Long Update computer 250 populates the work order database 130 GUI input fields with the parsed data value results of step 620. In an embodiment, the GUI input fields comprise a first text field for receiving a customer site address and a second text field for receiving a location. The work order database 130 "add record routine" then formats, via a formatter component, the parsed data values, comprising a site address and location, into a work order database record (i.e., a "second" record) at step 630 and adds or copies the formatted record to the work order database 130 at step 635, using an insertion means such as a write( ) utility function.

The Lat/Long Update computer 250 determines whether more records are present in the match file stored on diskette 240 at step 640. If more records are present, then the Lat/Long Update computer 250 increments a record pointer in step 645 and continues executing within the processing loop starting at step 620. When the Lat/Long Update computer 250 determines that no more records are present at step 640, the Lat/Long Update computer 250 exits processing at step 695.

In an embodiment, the match file contains completed records constructed from the incomplete customer site location records of the DMR 205. A follow-on processor provides subsequent processing of the match file data. For instance, in one embodiment the match file is used by a Lat/Long Update computer 250 to update records stored in a work order database 130.

These updates provide missing geographical location (i.e., latitude and longitude) values for customer sites that are associated with pending work orders. By supplying these missing latitude and longitude values for work order records in the work order database 130, the Lat/Long Update computer 250 enables an automated dispatcher 120 to automatically dispatch a technician to the customer site associated with the work order.

Various embodiments of the present invention have been described in fulfillment of the various objects of the invention. It should be recognized that these embodiments are merely illustrative of the principles of the present invention. Numerous modifications and adaptations thereof will be apparent to those skilled in the art without departing from the spirit and scope of the present invention.

What is claimed is:

1. A computer-implemented method comprising:
    receiving a file having an incomplete record, wherein the incomplete record comprises a key value and a null location;
    extracting the incomplete record from the file;
    extracting the key value from the incomplete record;
    searching a data repository for the key value, wherein a successful search yields a match record comprising the key value and a non-null location value;
    inserting the match record into a match file; and
    forwarding the match file to a follow-on processor that reforms the match file and merges match records with a work order database.

2. The method of claim 1, wherein the non-null location value comprises latitude and longitude coordinates.

3. The method of claim 1, wherein the key value comprises a street address.

4. The method of claim 1, wherein the key value comprises a cross-connect identifier.

5. The method of claim 1, wherein the key value comprises a wire center identifier.

6. The method of claim 1, wherein the key value comprises an allocation area identifier.

7. The method of claim 1, wherein the key value comprises at least two of a street address, a cross-connect identifier, a wire center identifier, and an allocation area identifier.

8. The method of claim 1, wherein the data repository comprises at least one database.

9. The method of claim 8, wherein the at least one database comprises a local database and a wire center database.

10. A computer-implemented system comprising:
    a receiver for a file having an incomplete record, wherein the incomplete record comprises a key value and a null location value;
    an extractor for extracting the incomplete record from the file;
    a parser for parsing the key value from the incomplete record;
    a data repository;
    a database server searching the data repository for the key value, wherein a successful search yields a match record comprising the key value and a non-null location value;
    a computer inserting the match record into a match file; and
    a follow-on processor receiving the match file, formatting the match file and merging match records with a work order database.

11. The system of claim 10, wherein the non-null location value comprises latitude and longitude coordinates.

12. The system of claim 10, wherein the key value comprises a street address.

13. The system of claim 10, wherein the key value comprises a cross-connect identifier.

14. The system of claim 10, wherein the key value comprises a wire center identifier.

15. The system of claim 10, wherein the key value comprises an allocation area identifier.

16. The system of claim 10, wherein the key value comprises at least two of a street address, a cross-connect identifier, a wire center identifier, and an allocation area identifier.

17. The system of claim 10, wherein the data repository comprises at least one database.

18. The system of claim 17, wherein the at least one database comprises a local database and a wire center database.

* * * * *